United States Patent [19]

Bombardelli et al.

[11] Patent Number: 5,264,591

[45] Date of Patent: Nov. 23, 1993

[54] BACCATINE III DERIVATIVES

[75] Inventors: Ezio Bombardelli; Bruno Gabetta, both of Milan, Italy

[73] Assignee: Indena S.P.A., Milan, Italy

[21] Appl. No.: 881,150

[22] Filed: May 11, 1992

[30] Foreign Application Priority Data

Mar. 6, 1992 [IT] Italy .............................. MI92 A 0528

[51] Int. Cl.$^5$ .......................................... C07D 305/14
[52] U.S. Cl. .................................... 549/214; 549/229; 549/358; 549/432; 549/510; 549/511
[58] Field of Search ............... 549/214, 229, 358, 432, 549/510, 511

[56] References Cited

U.S. PATENT DOCUMENTS 4,924,011  5/1990  Denis et al. ......................... 549/510

OTHER PUBLICATIONS

Journal of Liq. Chromatography, 12(11), pp. 2117–2132, 1989.

Primary Examiner—C. Warren Ivy
Assistant Examiner—Ba K. Trinh
Attorney, Agent, or Firm—Mathews, Woodbridge & Collins

[57] ABSTRACT

Isolation of a new taxane having pharmaceutical activity, la 14-beta-hydroxy-10-deacetyl-baccatine III and hemisynthesis of some derivatives useful as antitumor agents and intermediates.

8 Claims, No Drawings

BACCATINE III DERIVATIVES

The present invention concerns new taxans of formula 1, processes for their preparation and pharmaceutical uses thereof.

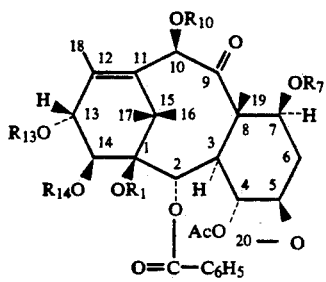

In the general formula 1, $R_1$ when taken individually is hydrogen; and $R_{14}$ when taken individually is hydrogen, tri(lower alkyl)silyl, or alkanoyl of 2 to 9 carbon atoms, unsubstituted or mono-, di-, or trisubstituted with halo or monosubstituted with phenyl which is unsubstituted or mono-, di-, or trisubstituted with halo, lower alkoxy, or lower haloalkoxy; or $R_1$ and $R_{14}$, when taken together, are carbonyl or lower alkylidene, unsubstituted or substituted with phenyl; each of $R_7$ and $R_{10}$ is hydrogen, tri(lower alkyl)silyl, or alkanoyl of 2 to 9 carbon atoms, unsubstituted or mono-, di-, or trisubstituted with halo or monosubstituted with phenyl which is unsubstituted or mono-, di-, or trisubstituted with halo, lower alkoxy, or lower haloalkoxy; and $R_{13}$ is hydrogen, trialkylsilyl, —CO-CHOHCH($C_6H_5$)NHCO$C_6H_5$, —CO-CHOHCH($C_6H_5$)NHCOOC($CH_3$)$_3$, alkanoyl of 2 to 9 carbon atoms, unsubstituted or mono-, di-, or trisubstituted with halo or monosubstituted with phenyl which is unsubstituted or mono-, di-, or trisubstituted with halo, lower alkoxy, or lower haloalkoxy;

Ac is acetyl.

The term lower alkyl denotes a univalent saturated branched or straight hydrocarbon chain containing from 1 to 8 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, and the like.

The term lower alkoxy denotes a lower alkyl group joined to the remainder of the molecule through an ethereal oxygen bond. Representative of such alkoxy groups are methoxy, ethoxy, propoxy, isopropoxy, butoxy, isobutoxy, sec-butoxy, tert-butoxy, pentoxy, isopentoxy, neopentoxy, tert-pentoxy, hexoxy, isohexoxy, heptoxy, octoxy, and the like.

The term lower alkylidene denotes a geminally divalent saturated branched or straight hydrocarbon chain containing from 1 to 8 carbon atoms. Representative of such alkylidene groups are methylidene, ethylidene, propylidene, isopropylidene, butylidene, isobutylidene, pentylidene, neopentylidene, hexylidene, heptylidene, octylidene, and the like.

Representative lower haloalkoxy groups are difluoromethoxy, trifluoromethoxy.

The compound of formula 1 wherein $R_1=R_7=R_{10}=R_{13}=R_{14}=H$ (1a) is a new taxane which can be isolated substantially free of other compounds from vegetative material of the genus Taxus, particularly from the aereal parts of Taxus wallichiana.

This species is widespread in Asia, particularly on the himalayan cliffs. The structure 1a has been assigned to the new taxane by means of NMR ($^1H$ and $^{13}C$—NMR) studies and of X-rays difractometric analysis. It comprises an additional hydroxy groups, in position 14$\beta$, in comparison with 10-deacetylbaccatine III, known synthon used for the synthesis of the antitumor agents taxol and taxoter. The presence of this additional hydroxy groups imparts to the molecule an higher hydrophilicity than that of 10-deacetylbaccatine III itself, with consequent advantages in connection with the administration by perfusion in humans of antitumor drugs containing this kind of diterpenic nucleus.

The new taxane 1a can be isolated from the vegetable material, preferably from the needles, by means of two different extraction processes.

It is in fact possible to extract the vegetable material either with a water miscible or with immiscible solvents. In the first case (Method A), a protic solvent such as methanol or ethanol may be used alone or in combination with water. A medium polar aprotic solvent such as acetone, alone or mixed with water, also can be used. 1a is extracted from the vegetable material with these solvents at room temperature. The obtained extract is concentrated until removal of the organic solvent, filtered from the formed insoluble material and then treated with a water immiscible solvent, e.g. ethyl acetate or a chlorinated solvent, preferably methylene chloride. The organic extract containing 1a is then evaporated to dryness and the obtained residue is purified by column chromatography. When a water immiscible solvent is used instead (Method B), an aromatic hydrocarbon, e.g. benzene or toluene, or a chlorinated solvent, e.g. methylene chloride, chloroform, 1,2-dichloroethane, 1,1,1-trichloroethane, can be used. In this case, the extraction of the vegetable material is carried out at room temperature or at the reflux temperature of the chosen solvent.

The obtained extract is concentrated, purified from polar impurities by treatment with an hydroalcoholic mixture, for instance 30% hydromethanolic, and evaporated to dryness.

The residue, similarly to that obtained with the Method A, is then subjected to further purification by column chromatography.

By both processes, the residue obtained from the two different extractions of the vegetable material is purified by silica gel column chromatography eluting with solvent mixtures such as cyclohexane acetone, methylene chloride ethyl acetate or methylene chloride methanol, adjusting the ratios of these mixtures so as to isolate the largest possible amount of 1a. Depending on the quality of the starting vegetable material, yields in 1a ranging from 0.1 to 0.01% are obtained. The chromatographic fractions containing 1a are pooled, evaporated to dryness and the residue is crystallized from methanol, ethyl acetate, acetone or acetonitrile to give pure 1a.

The compounds 1 can be prepared from 1a according to known methods.

Partially derivatized products may be obtained from 1a since the hydroxy groups have the following reactivity order: 7-OH>10-OH>14-OH>13-OH.

Therefore, either by using suitable amounts of reagents, or by suitably adjusting the temperature and the reaction time, partially derivatized compounds may be obtained.

The compounds wherein all or some of the $R_7$, $R_{10}$, $R_{13}$, $R_{14}$ are an alkanoyl group of 2 to 9 carbon atoms as defined above, can be obtained by reacting 1a or a derivative thereof with a carboxylic acid anhydride of formula $R_5$—COO—CO—$R_5$, wherein $R_5$ is an alkyl group of 1 to 8 carbon atoms unsubstituted or mono-, di-, or trisubstituted with halo or monosubstituted with phenyl which is unsubstituted or mono-, di-, or trisubstituted with halo, lower alkoxy, or lower haloalkoxy, or with an equivalent derivative in the presence of a 4-aminosubstituted aminopyridine and in a suitable solvent.

The acylation reaction can be carried out at room temperature or optionally by refluxing the reaction mixture.

Alternatively, 1a or a derivative thereof can be treated with an acid $R_5CO_2H$ in chlorinated solvent such as methylene chlorinated or chloroform in the presence of a carbodiimide such as dicyclohexylcarbodiimide or 1-(3-dimethylaminopropyl)-3-ethylcarbodiimide and of a catalyst such as 4-(N,N-dimethylamino)-pyridine or 4-(pyrrolidino) pyridine at room temperature or at the solvent reflux.

The compound 1 wherein the $R_7$, $R_{10}$, $R_{13}$, $R_{14}$ groups are a tri(loweralkyl)silyl group can be obtained from 1a or from a derivative thereof by treatment with a silylating agent in a suitable solvent and in presence of suitable catalysts. For instance, t-butyldimethylchlorosilane can be used in the amount of 1.1 equivalents for each OH group to be reacted, in the presence of 2.2 equivalents of imidazole or of 4-(N,N-dimethylamino)pyridine in dimethylformamide and at room temperature.

The compounds of formula 1 wherein the groups $R_1$ and $R_{14}$ taken together form a CO group may be prepared by reacting 1a and a suitable chloroformate in a basic solvent, e.g. pyridine. For instance, by reacting 1a with an excess of trichloroethylchloroformate in pyridine at 80° C. for some minutes, the acylation with the —COOCH$_2$CCl$_3$ group of the hydroxy groups in the positions 7, 10, 14, is obtained.

However, in the reaction medium an intramolecular nucleophilic substitution between the substituent in 14 and the hydroxy group in position 1 takes place, yielding the carbonate 1b.

The derivatives of formula 1, wherein $R_1$ and $R_{14}$ taken together form a lower alkylidene unsubstituted or substituted with phenyl, may be prepared by reacting 1a with an aldehyde or a ketone, in suitably catalyzed conditions. For instance, by treating 1a with 2,2-dimethoxypropane in acetone solutions and in the presence of pyridine p-toluenesulfonate, the cyclic ketone 1c is obtained, involving in its formation the hydroxy groups in the positions 14 and 1 of 1a.

The compounds of the present invention of formula 1 have antimitotic activity comparable to that of known taxanes such as taxol or derivatives thereof, and in vivo, antitumor activity.

In vitro, they exibited activity on the brain tubuline (Shelanski, Proc. Natl. Acad. Sci. USA, 70, 765, 1973) and on human cultured leucocytes. The compounds of the invention have an activity on tubuline which is twice that of the corresponding derivatives of baccatine III.

The compounds can be administered orally or parenterally, alone or in combination with other therapeutic agents including anti-neoplastic agents, steroids, etc., to a mammal in need of such treatment. Parenteral routes of administration include intramuscular, intrathecal, intravenous and intraarterial. As with any drug of this type, dosage regimens must be titrated to the particular neoplasm, the condition of the patient, and the response observed but generally doses will be from about 10 to about 30 mg/m$^2$ per day for 5 days or 150 to 250 mg/m$^2$ given once every three weeks. While having a low toxicity as compared to other agents now in use, a toxic response often can be eliminated by either or both of reducing the daily dosage or administering the compound on alternative days or at longer intervals such as every three to five days. Oral dosage forms include tablets and capsules containing from 1–10 mg of drug per unit dosage. Isotonic saline solutions containing 20–100 mg/ml can be used for parenteral administration.

The following examples will further exemplify the invention.

EXAMPLE 1

Isolation of 14-hydroxy-10-deacetyl-baccatine III 1a (1, $R_1=R_7=R_{10}=R_{13}=R_{14}=H$) from *Taxus wallichiana* Leaves

Method A 1 kg of *Taxus wallichiana* leaves, vacuum-dried at 35° C., were finely ground and extracted with 6 portions of methanol, 3 1 each, under stirring at room temperature, each extraction being carried out for 6 hours. The collected extracts were concentrated under reduced pressure to a volume of 1 1, left to stand for 24 hours and the insoluble material was filtered off. The filtrate was extracted 6 times with 500 ml of methylene chloride. The collected organic phases were vacuum concentrated to 500 ml and the resulting solution was purified through a chromatographic column containing 300 g of silica gel, using methylene chloride as eluent until the complete elimination of apolar compounds, subsequently using a methylene chloride-ethyl acetate 85:15 mixture, thus eluting pure 1a. The collected fractions were vacuum concentrated to dryness. The residue was crystallized from 7 volumes of methanol. The crystallized solid was pump-filtered, washed with a small amount of methanol and vacuum-dried at 40° C. 800 mg of 1a were obtained, m.p. 215°–217° C., M+ at m/z 560.

Elemental analysis for $C_{29}H_{36}O_{11}$: Found: C, 62.07; H, 6.53%; Theoretical: C, 62.13; H, 6.47%.

EXAMPLE 2

Isolation of 14-hydroxy-10-deacetyl-baccatine III 1a 1, $R_1.R_7=R_{10}=R_{13}=R_{14}=H$) from *Taxus wallichiana* Leaves

Method B 1 kg of *Taxus wallichiana* leaves, vacuum-dried at 35° C., were finely ground and extracted with 6 portions of toluene, 3 1 each, under stirring at room temperature, each extraction being carried out for 6 hours. The collected extracts were concentrated under reduced pressure to a volume of 500 ml and treated with 3 portions, 70 ml each, of 20% aqueous methanol. The toluene phase was vacuum concentrated to dryness and the residue was dissolved in 500 ml of methylene chloride. The obtained solution was purified by column chromatography as described in Example 1 to give pure 1a; m.p. 215°–217° C.

EXAMPLE 3

Preparation of 1b (1, $R_7=R_{10}=-COOCH_2CCl_3$, $R_{13}=H$, $R_1$ and $R_{14}$ Taken Together are CO)

300 mg of 1a (0.53 mmoles) were dissolved in 6 ml of anhydrous pyridine and treated for 5 minutes at 80° C. with 0.49 ml (3.41 mmoles) of trichloroacetylchloroformate. The reaction mixture was cooled down to room temperature, then some drops of methanol were added to destroy reagent excess. The reaction mixture was diluted with water and extracted with methylene chloride. The organic phase was separated, washed with dilute hydrochloric acid, dried over sodium sulfate and concentrated to dryness. The residue was purified through a chromatographic column containing 7 g of silica gel, eluting with a 1:1 hexane-ethyl acetate mixture. 295 mg (59%) of 1b were obtained. M+ (C.I.MS) at m/z 955 (937+NH4).

Elemental analysis for: $C_{36}H_{35}O_{16}Cl_6$: Found: C, 45.98; H, 3.91; Cl 22.67%; Theoretical: C, 46.10; H, 3.84; Cl 22.73%.

EXAMPLE 4

Preparation of 1c (1, $R_7=R_{10}=R_{13}=H$; $R_{14}$ and $R_1$ Taken Together are $C(CH_3)_2$))

100 mg of 1a were dissolved in 17 ml of acetone, previously distilled over copper sulfate, and treated with 7 ml of 2,2-dimethoxypropane and 150 mg of pyridine p-toluenesulfonate, while stirring at room temperature. The reaction mixture was then evaporated to dryness and the residue was recovered with methylene chloride. The organic solution was washed with water to remove pyridinium salt, dryed over sodium sulfate and the solvent was distilled off under reduced pressure. The residue was purified through a chromatographic column containing 5 g of silica gel, using ethyl ether as eluent. 82 mg (76%) of 1c were obtained; m.p. 166°-170° C., M+ (C.I.MS) at m/z 618 (600+NH4).

Elemental analysis for $C_{32}H_{40}O_{11}$: Found: C, 63.89; H, 6.71%; Theoretical: C, 64.00; H, 6.67%.

EXAMPLE 5

Preparation of 14-β-hydroxy-10-deacetyl-7,10-dichloro acetate baccatine III (1, $R_1=R_{13}=R_{14}=OH$; $R_7=R_{10}=COCHCl_2$)

200 mg of 1a were dissolved in 3 ml of anhydrous pyridine and treated at room temperature for 24 hours with 160 microliters of dichloroacetic anhydride and 10 mg of 4(N,N-dimethylammino)pyridine.

The reaction mixture was diluted with ice-water and extracted with chloroform. The organic phase was washed with diluted hydrochloric acid, then with water dried over sodium sulfate and evaporated to dryness.

The residue was purified with silica gel column chromatography eluting with a 3:7 hexane-ethyl acetate mixture. 217 mg of 7,10-dichloroacetate were obtained and crystallized from chloroform, M+792.

Elemental analysis for $C_{33}H_{36}O_{13}Cl_4$: Found: C, 49.86; H, 4.71; Cl, 17.01%; Theoretical: C, 50.00; H, 4.54; Cl, 17.93%.

We claim:

1. A compound of the formula:

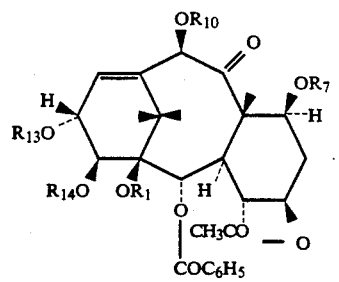

wherein
(1) (a) $R_1$ and $R_{14}$, when taken together, are carbonyl or lower aklylidene, unsubstituted or substituted with phenyl; or
(1) (b) (i) $R_{14}$, when taken independently of $R_1$, is hydrogen,
tri-(lower alkyl)silyl, or
alkanoyl of 2 to 9 carbon atoms, unsubstituted, monosubstituted, disubstituted, or trisubstituted with halo, or nomosubstituted with phenyl which in turn is unsubstituted, monosubstituted, disubstituted, or trisubstituted with halo, lower alkoxy, or lower haloalkoxy, and
(1) (b) (ii) $R_1$, when taken independently of $R_{14}$, is hydrogen;
(2) each of $R_7$ and $R_{10}$, independently of the other, is hydrogen,
tri-(lower alkyl-silyl, or
alkanoyl of 2 to 9 carbon atoms, unsubstituted, monosubstituted, disubstituted, or trisubstituted with halo, or nomosubstituted with phenyl which in turn is unsubstituted, monosubstituted, disubstituted, or trisubstituted with halo, lower alkoxy, or lower haloalkoxy, and
(3) $R_{13}$ is
hydrogen,
tri-(lower alkyl)silyl,

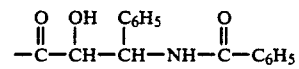

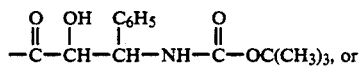

alkanoyl of 2 to 9 carbon atoms, unsubstituted, monosubstituted, disubstituted, or trisubstituted with halo, or nomosubstituted with phenyl which in turn is unsubstituted, monosubstituted, disubstituted, or trisubstituted with halo, lower alkoxy, or lower haloalkoxy;
at least one of $R_7$, $R_{10}$, $R_{13}$ and $R_{14}$ being a group other than hydrogen.

2. A compound according to claim 1 wherein $R_7$ is alkanoyl of 2 to 9 carbon atoms, unsubstituted, monosubstituted, disubstituted, or trisubstituted with halo, or nomosubstituted with phenyl which in turn is unsubstituted, monosubstituted, disubstituted, or trisubstituted with halo, lower alkoxy, or lower haloalkoxy.

3. A compound according to claim 1 wherein $R_{10}$ is alkanoyl of 2 to 9 carbon atoms, unsubstituted, monosubstituted, disubstituted, or trisubstituted with halo, or nomosubstituted with phenyl which in turn is unsubstituted, monosubstituted, disubstituted, or trisubstituted with halo, lower alkoxy, or lower haloalkoxy.

4. The compounds according to claim 1 wherein $R_1$ and $R_{14}$ together are carbonyl, each of $R_7$ and $R_{10}$ is trichloroacetyl, and $R_{13}$ is hydrogen.

5. The compound according to claim 1 wherein $R_1$ and $R_{14}$ together are isoproplidene and each of $R_7$, $R_{10}$, and $R_{13}$ is hydrogen.

6. The compound according to claim 1 wherein each of $R_1$, $R_{13}$, and $R_{14}$ is hydrogen are isopropylidene and each of $R_7$ and $R_{10}$ is dicloroacetyl.

7. An antineoplastic composition comprising an effective amount of a compound according to claim 1 in combination with a pharmaceutically acceptable carrier.

8. The method of effecting an antineoplastic effect in a mammal in need thereof which comprises administering thereto an effective amount of a compound according to claim 1.

* * * * *